(12) United States Patent
Mohan Rao et al.

(10) Patent No.: US 9,000,221 B2
(45) Date of Patent: Apr. 7, 2015

(54) PROCESSES FOR THE PREPARATION OF 4'-[3-[4-(6-FLUORO-1,2-BENZISOXAZOL-3-YL)PIPERIDINO]PROPOXY]-3'-METHOXYACETOPHENONE AND INTERMEDIATES THEREOF

(75) Inventors: Dodda Mohan Rao, Hyderabad (IN); Pingili Krishna Reddy, Hyderabad (IN); Buthukuri Venkat Reddy, Hyderabad (IN)

(73) Assignee: Symed Labs Limited (IN)

( * ) Notice: Subject to any disclaimer, the term of this patent is extended or adjusted under 35 U.S.C. 154(b) by 56 days.

(21) Appl. No.: 13/575,250

(22) PCT Filed: Jul. 18, 2011

(86) PCT No.: PCT/IN2011/000473
§ 371 (c)(1),
(2), (4) Date: Jul. 25, 2012

(87) PCT Pub. No.: WO2012/032532
PCT Pub. Date: Mar. 15, 2012

(65) Prior Publication Data
US 2013/0190501 A1    Jul. 25, 2013

(30) Foreign Application Priority Data

Sep. 7, 2010 (IN) .......................... 2610/CHE/2010
Dec. 24, 2010 (IN) .......................... 3959/CHE/2010

(51) Int. Cl.
C07C 45/00     (2006.01)
C07C 315/04    (2006.01)
C07D 261/20    (2006.01)
C07C 45/29     (2006.01)
C07C 303/30    (2006.01)
C07D 413/04    (2006.01)

(52) U.S. Cl.
CPC ............ *C07C 315/04* (2013.01); *C07D 261/20* (2013.01); *C07C 45/004* (2013.01); *C07C 45/292* (2013.01); *C07C 303/30* (2013.01); *C07D 413/04* (2013.01)

(58) Field of Classification Search
CPC ....................................................... C07C 45/71
USPC ........................................................ 568/315
See application file for complete search history.

(56) References Cited

U.S. PATENT DOCUMENTS

| | | | |
|---|---|---|---|
| 5,364,866 A * | 11/1994 | Strupczewski et al. | 514/321 |
| RE39,198 E | 7/2006 | Strupczewski et al. | |
| 7,977,356 B2 | 7/2011 | Grimler et al. | |
| 8,198,305 B2 | 6/2012 | Harbeson | |
| 2007/0197595 A1 | 8/2007 | Nozulak et al. | |
| 2008/0027041 A1 | 1/2008 | Hudkins et al. | |

FOREIGN PATENT DOCUMENTS

| | | | |
|---|---|---|---|
| EP | 0402644 B1 | | 8/1995 |
| WO | WO 2011/061750 | * | 5/2011 |

* cited by examiner

*Primary Examiner* — John Mabry
(74) *Attorney, Agent, or Firm* — Caesar, Rivise, Bernstein, Cohen & Pokotilow, Ltd.

(57) ABSTRACT

The present invention relates to processes for the preparation of 4'-[3-[4-(6-fluoro-1,2-benzisoxazol-3-yl)piperidino]propoxy]-3'-methoxyacetophenone and intermediates thereof. The present invention also provides a process for purifying 4'-[3-[4-(6-fluoro-1,2-benzisoxazol-3-yl)piperidino]propoxy]-3'-methoxyacetophenone to obtain the purity greater than about 98.0 area % to about 99.0 area % as measured by HPLC, preferably greater than about 99.0 area % to about 99.5 area %, more preferably greater about 99.5 area % to about 99.9 area %. individual impurities lower than about 0.15 area %, preferably lower than about 0.1% and total impurities lower than about 0.5 area % by HPLC.

4 Claims, 1 Drawing Sheet

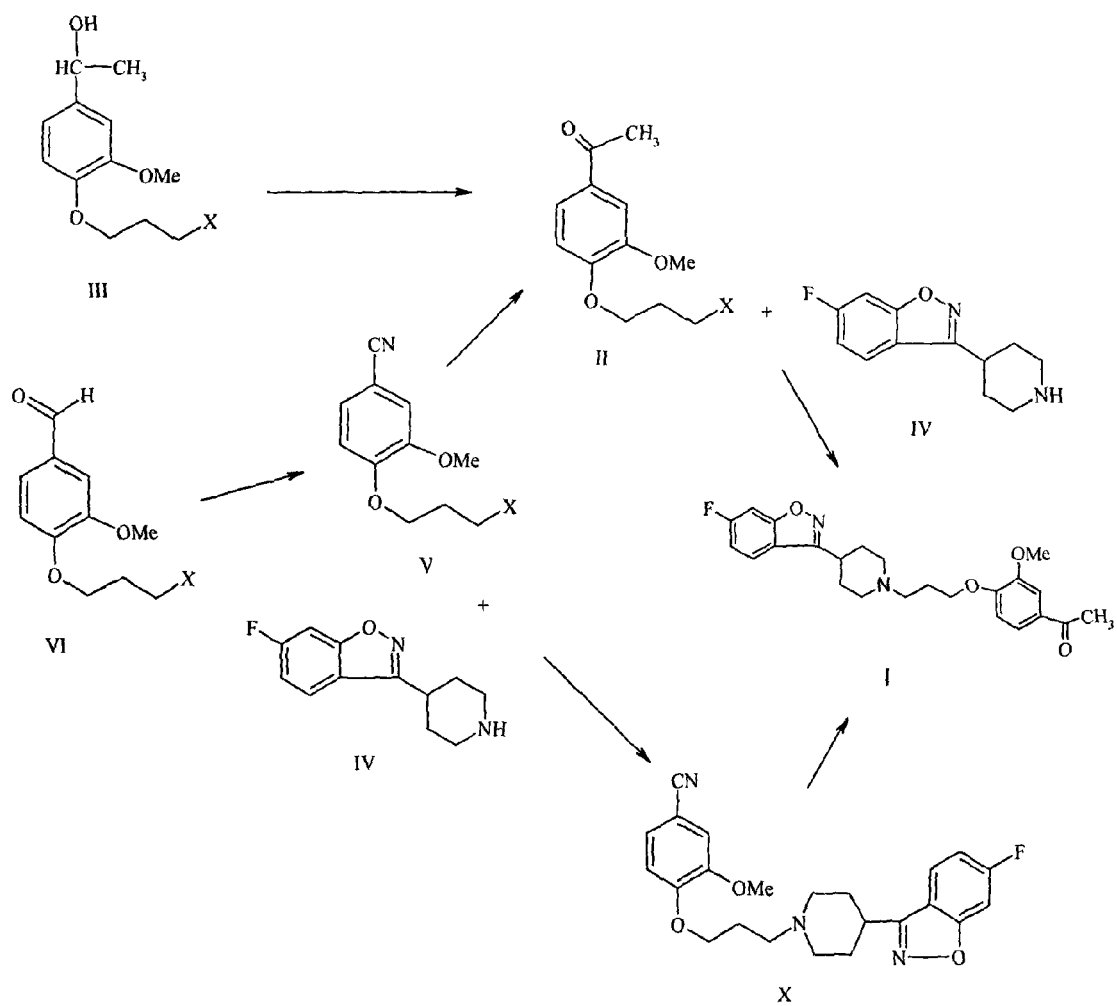

PROCESSES FOR THE PREPARATION OF 4'-[3-[4-(6-FLUORO-1,2-BENZISOXAZOL-3-YL)PIPERIDINO]PROPOXY]-3'-METHOXYACETOPHENONE AND INTERMEDIATES THEREOF

PRIORITY

This application claims the benefit of Indian Provisional Applications with no. 2610/CHE/2010, filed on 7 Sep. 2010 and 3959/CHE/2010, filed on 24 Dec. 2010, the contents of each of which are incorporated by reference herein.

BACKGROUND OF THE INVENTION

1. Technical Field

The present invention relates to processes for the preparation of 4'-[3-[4-(6-fluoro-1,2-benzisoxazol-3-yl)piperidino]propoxy]-3'-methoxyacetophenone and intermediates thereof.

2. Description of the Related Art

Iloperidone is a neuroleptic and 5-hydroxytryptamine 2A antagonist to be used for the treatment of schizophrenia and general psychosis. Iloperidone is available in the market under the brand name FANAPT® in the form of tablets in the dosage strengths 1 mg, 2 mg, 4 mg, 6 mg, 8 mg, 10 mg, or 12 mg. Iloperidone is chemically known as 4'-[3-[4-(6-Fluoro-1,2-benzisoxazol-3-yl)piperidino]propoxy]-3'-methoxyacetophenone (herein after referred by its generic name Iloperdione) and represented by the structural formula I

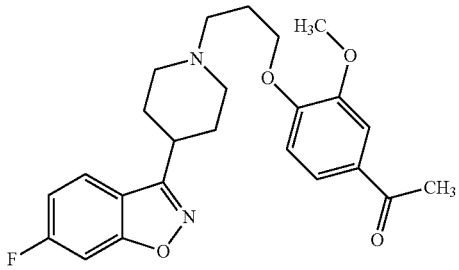

U.S. Pat. No. RE39198 E (U.S. Pat. No. 5,364,866) describes piperidinyl-benzisoxazole derivatives, including iloperidone, a pharmaceutical composition, a method of treatment, and a process for the preparation of iloperidone.

The described prior art processes uses expensive and hazardous chemicals rendering the processes expensive and not viable on commercial scale thus prompting a need for an improved process for the preparation of iloperidone and its intermediates, which avoids the use of hazardous and expensive chemicals, the likely formation of process related impurities.

The preparation of intermediate compound of formula II from novel compounds of formula III and V have not been reported in the literature as of now.

The reported prior art processes uses expensive and hazardous chemicals rendering the processes expensive and not viable on commercial scale. Hence there is a need in the art to provide an improved process for the preparation of iloperidone and its intermediates, which avoids the use of hazardous and expensive chemicals, the likely formation of process related impurities resulting in high yields and purities of the final products.

The applicant has now developed a new industrial synthesis which, in reproducible manner and without requiring laborious purification, yields iloperidone having a purity that is compatible with its use as a pharmaceutical active ingredient, starting from a intermediates obtained from simple and cost effective processes.

The processes of present invention are simple, eco-friendly, inexpensive, reproducible, robust and is well suited on an industrial scale.

SUMMARY OF THE INVENTION

The present invention relates to processes for the preparation of 4'-[3-[4-(6-fluoro-1,2-benzisoxazol-3-yl)piperidino]propoxy]-3'-methoxyacetophenone and intermediates thereof.

In one aspect, the present invention provides a process for preparing intermediate 4-($3^1$-sub-propoxy)-3-methoxy acetophenone compound of formula (II),

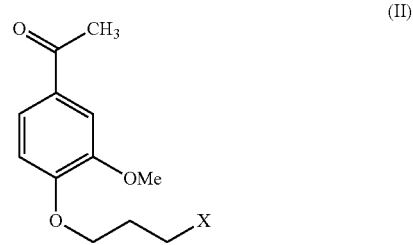

Where X is a leaving group selected from halogen, methanesulphonate, benzene sulphonate, p-toluenesulphonate, 4-nitrobenzene sulphonate, 4-bromobenzene sulphonate and trifluoromethyl sulphonate
comprising:
reacting a novel compound 1-[4-($3^1$-propoxy)-3-methoxy phenyl]ethanol of formula (III),

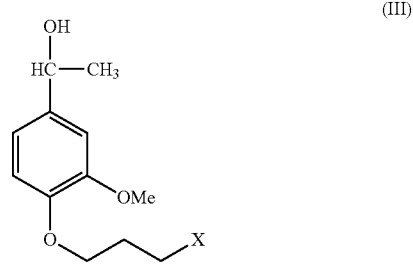

Where X is same as defined above.
with a suitable oxidizing agent optionally in the presence of an organic solvent.

In another aspect, the present invention provides another process for preparing intermediate 4-($3^1$-sub-propoxy)-3-methoxy acetophenone compound of Formula II,

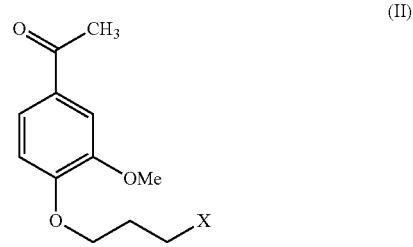

Where X is a leaving group selected from halogen, methanesulphonate, benzene sulphonate, p-toluenesulphonate, 4-nitrobenzene sulphonate, 4-bromobenzene sulphonate and trifluoromethyl sulphonate.

comprising:

a) reacting a compound 4-(3¹-sub-propoxy)-3-methoxy benzaldehyde of Formula VI,

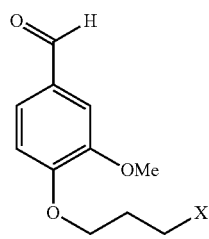

VI

Where X is same as defined above.

with a suitable reagent in the presence or absence of an organic solvent to give the compound 4-(3¹-sub-propoxy)-3-methoxybenzonitrile of Formula V

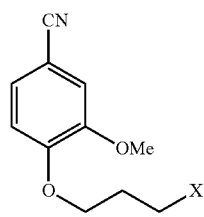

V

Where X is same as defined above.

b) reacting the compound of formula V with a Grignard reagent followed by treating the intermediate obtained with an acid to give the intermediate compound of formula II.

c) the conversion of compound of formula V to compound of formula II is also carried out in the presence of catalyst cuprous (I) salts.

In another aspect, the present invention relates to a process for the preparation of Iloperidone of formula I

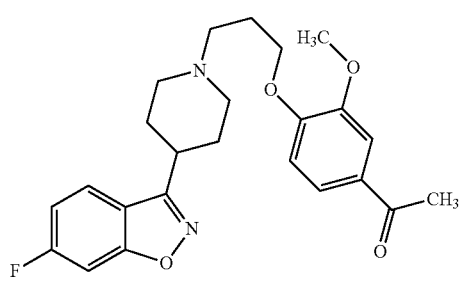

I comprising:

reacting the intermediate compound 4-(3¹-sub-propoxy)-3-methoxy acetophenone of formula (II)

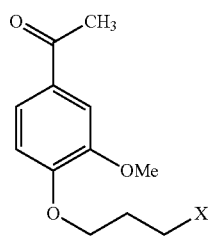

II

Where X is same as defined above.

with a compound 6-fluoro-3(4-piperidinyl)-1,2-benzisoxazole or a salt thereof of formula (IV)

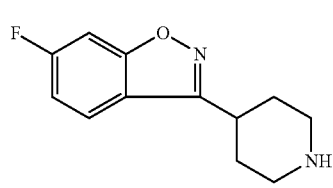

(IV)

in the presence of a base and a solvent.

In yet another aspect, the present invention provides an alternate process for the preparation of Iloperidone of formula I

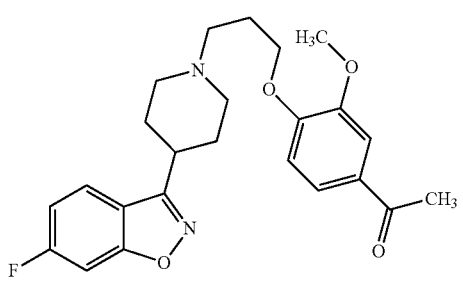

I comprising:

a) reacting the intermediate compound 4-(3¹-sub-propoxy)-3-methoxybenzonitrile of Formula (V)

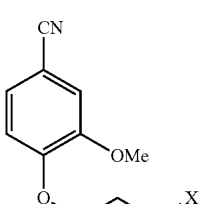

(V)

Where X is same as defined above.

with a compound 6-fluoro-3(4-piperidinyl)-1,2-benzisoxazole or a salt thereof of formula (IV)

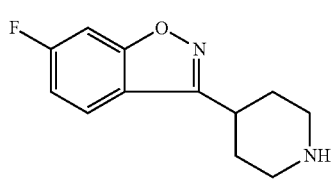

(IV)

in the presence of a base and an organic solvent to give 4'-[3-[4-(6-Fluoro-1,2-benzisoxazol-3-yl)piperidino]propoxy]-3'-methoxy benzonitrile of formula X

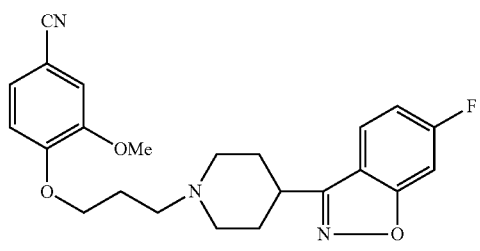

X b) reaction of the compound of formula X with Grignard reagents in the presence of catalyst cuprous (I) salts to afford compound of formula I.

In yet another aspect, the present invention provides a process for purifying iloperidone thereof comprising: a) providing a solution or suspension of iloperidone in a solvent or a mixture of solvents or their aqueous mixtures and b) precipitating the solid from the solution, and c) recovering the iloperidone in pure form.

In yet another aspect, the present invention provides iloperidone obtained by the processes herein described above having purity greater than about 98.0 area % to about 99.0 area % as measured by HPLC, preferably greater than about 99.0 area % to about 99.5 area %, more preferably greater about 99.5 area % to about 99.9 area %.

In yet further aspect, the present invention provides iloperidone obtained by the processes herein described above having individual impurities lower than about 0.15 area %, preferably lower than about 0.1% and total impurities lower than about 0.5 area % by HPLC.

In another aspect, the present invention provides Iloperidone having the compound 4-hydroxy-3-methoxy benzaladehyde of structural formula VII

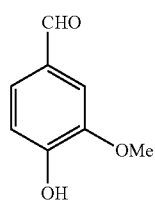

VII in an amount less than or equal to 0.10 area % as measured by HPLC.

In another aspect, the present invention provides Iloperidone having the compound 4-(3-chloropropoxy)-3-methoxy benzaladehyde of structural formula VIII

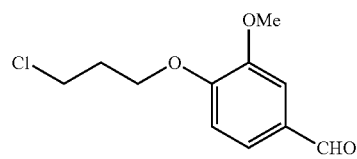

VIII in an amount less than or equal to 0.10 area %, as measured by HPLC.

In yet another aspect, the present invention provides Iloperidone having the compound 4-(3-chloropropoxy)-3-methoxy acetophenone of structural formula IX

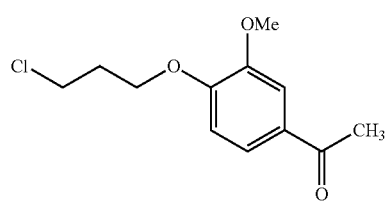

IX in an amount less than or equal to 0.10 area % as measured by HPLC.

In yet further aspect, the present invention provides Iloperidone having the compound 6-fluoro-3-(4-piperidinyl)-1,2-benzisoxazole or a salt thereof of structural formula IV

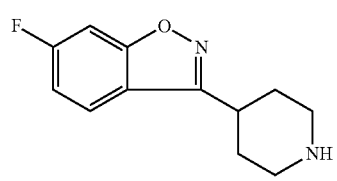

IV in an amount less than or equal to 0.10 area % as measured by HPLC.

BRIEF DESCRIPTION OF THE DRAWING

FIG. 1: is a schematic representation of the processes of present invention.

DETAILED DESCRIPTION OF THE INVENTION

The present invention relates to processes for the preparation of 4'-[3-[4-(6-fluoro-1,2-benzisoxazol-3-yl)piperidino]propoxy]-3'-methoxyacetophenone and intermediates thereof.

In one embodiment, the present invention provides a process for preparing intermediate 4-(3¹-sub-propoxy)-3-methoxy acetophenone compound of formula (II),

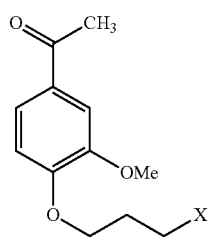

(II)

Where X is a leaving group selected from halogen, methanesulphonate, benzene sulphonate, p-toluenesulphonate, 4-nitrobenzene sulphonate, 4-bromobenzene sulphonate and trifluoromethyl sulphonate comprising:
reacting a novel compound 1-[4-($3^1$-propoxy)-3-methoxy phenyl]ethanol of formula (III),

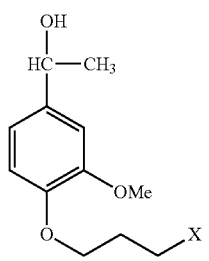

(III)

Where X is same as defined above
with a suitable oxidizing agent optionally in the presence of an organic solvent.

The oxidizing agents that can be used include but are not limited to pyridinium dichromate, collin's reagent, pyridinium chlorochromate, pyridinium chlorochromate on alumina, DMSO-DCC, DMSO-acetic anhydride and the like; or mixtures thereof. Preferably DMSO-DCC or DMSO-acetic anhydride.

The molar ratio of oxidizing agent to the compound of formula (III) can be from about 5:1 to about 1:1, preferably 1:1.

The solvents that can be used include but are not limited to water, halogenated solvents such as dichloromethane, ethylene dichloride, chloroform, chlorobenzene and the like; esters such as ethyl acetate, isopropyl acetate, tertiary butyl acetate and the like; hydrocarbon solvents such as n-heptane, cyclohexane, n-hexane, toluene, xylene and the like; ethers such as tetrahydrofuran, 1,4-dioxane and the like; aprotic polar solvents such as N,N-dimethylformamide (DMF), dimethylsulfoxide (DMSO), N,N-dimethylacetamide (DMA), N-methyl pyrrolidine (NMP) and the like; or mixtures thereof in various proportions without limitation. Preferably, water or halogenated solvent dichloromethane is being used.

The conversion of compound of formula III to the compound of formula II is optionally carried out in the absence of solvents.

The conversion of compound of formula III to the compound of formula II is carried out in the presence of an acid when DMSO-DCC is being used as oxidizing agent.

The acid that can be used include, but are not limited to hydrochloric acid, hydrobromic acid, hydroiodic acid, nitric acid, sulfuric acid, phosphoric acid and the like, and their aqueous mixtures thereof, preferably ortho phosphoric acid or trifluoro acetic acid.

The oxidation of compound of formula III to the compound of formula II is carried out using DMSO-DCC as oxidizing agent in the presence of pyridinium trifluoroacetate.

The reaction time and the temperature should be suitable to bring the reaction to completion at a minimum time, without the production of unwanted side products. In general, it is convenient to carry out the reaction at a temperature of from about 20° C. to about 100° C., preferably at a temperature of from about 25° C. to about 35° C. The time required for the reaction may also vary widely, depending on many factors, notably the reaction temperature and the nature of the reagent and solvent employed. However, provided that the reaction is effected under the preferred conditions discussed above, a period of from about 1 hour to about hours, preferably from about 1 hour to 5 hours is sufficient.

The intermediate compound of formula II is optionally dried under conditions which avoid degradation of the product, which can be from about 25° C. to about 40° C. in the presence or absence of reduced pressure.

The processes reported for the preparation of Iloperdione or its intermediates results formation of various impurities and bye products leading to several purification steps thus resulting in very poor yields and purities of the intermediates and final product.

Advantageously, the processes of present invention provides the intermediate compound of formula II from novel intermediate compound of formula III and also further conversion to compound of formula I in higher yields and purities which inturn results in higher yields and purities of final product.

The intermediate compound of formula II may be obtained in crystalline or amorphous form.

The compound of formula III used herein can be prepared by the processes known in the art.

The intermediate compound of formula II is purified by recrystallisation, using a solvent or mixture of solvents; such as aqueous methanol, ethanol, isopropyl alcohol, n-hexane, aqueous N,N-dimethyl formamide, cyclohexane, acetone, acetonitrile and mixtures thereof.

In one embodiment of the present invention, there is provided a process for preparation of intermediate 1-[4-($3^1$-chloropropoxy)-3-methoxyphenyl]ethanone compound of Formula II,

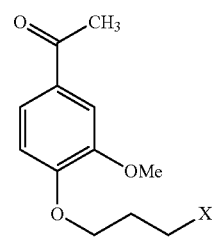

II

Where X is a leaving group selected from halogen, methanesulphonate, benzene sulphonate, p-toluenesulphonate, 4-nitrobenzene sulphonate, 4-bromobenzene sulphonate and trifluoromethyl sulphonate.

comprising:
a) reacting a compound 4-($3^1$-Chloropropoxy)-3-methoxy benzaldehyde of Formula VI,

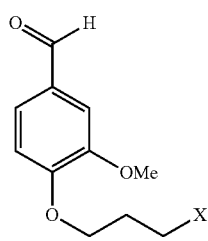

Where X is same as defined above.

with a suitable reagent in the presence of an organic solvent to give the compound 4-(3¹-chloropropoxy)-3-methoxybenzonitrile of Formula V

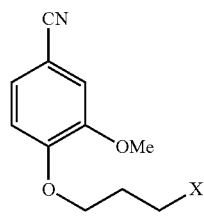

Where X is same as defined above.

b) reacting the compound of formula V with a Grignard reagent followed by treating the intermediate obtained with an acid in the present of an organic solvent to give the desired intermediate compound of formula II.

c) The conversion of compound of formula V to compound of formula II is also carried out in the presence of catalyst cuprous (I) salts.

The reagent that can be used in step a) include but are not limited to hydroxyl amine hydrochloride or hydroxyl amine sulphate. Preferably hydroxyl amine hydrochloride.

The molar ratio of the reagent to the compound of formula (VI) can be from about 5:1 to about 1:1, preferably 1:1.

The intermediate obtained is treated with acetic anhydride or sodium formate and formic acid or sodium acetate and acetic acid to give the compound of formula V.

The solvents that can be used in step a) include but are not limited to water, alcohols such as methanol, ethanol, isopropyl alcohol, n-butanol and the like; halogenated solvents such as dichloromethane, ethylene dichloride, chloroform, chlorobenzene and the like; esters such as ethyl acetate, isopropyl acetate, tertiary butyl acetate and the like; hydrocarbon solvents such as n-heptane, cyclohexane, n-hexane, toluene, xylene and the like; ethers such as tetrahydrofuran, 1,4-dioxane and the like; aprotic polar solvents such as N,N-dimethylformamide (DMF), dimethylsulfoxide (DMSO), N,N-dimethylacetamide (DMA), N-methyl pyrrolidine (NMP) and the like; or mixtures thereof in various proportions without limitation. Preferably, ethanol is being used.

The reaction time and the temperature should be suitable to bring the reaction to completion at a minimum time, without the production of unwanted side products. In general, it is convenient to carry out the reaction at a temperature of from about 35° C. to about reflux temperatures of the reaction mixture or the solvents used. Preferably at a temperature of from about 45° C. to about reflux temperatures. The time required for the reaction may also vary widely, depending on many factors, notably the reaction temperature and the nature of the reagent and solvent employed. However, provided that the reaction is effected under the preferred conditions discussed above, a period of from about 30 minutes to about 10 hours, preferably from about 1 hour to about 4 hours is sufficient.

The solvents that can be used in step b) grignard reaction include but are not limited to hydrocarbon solvents such as n-heptane, cyclohexane, n-hexane, toluene, xylene and the like; ethers such as diethyl ether, tetrahydrofuran, 1,4-dioxane and the like; or mixtures thereof in various proportions without limitation. Preferably, ether or toluene is being used.

The reaction time and the temperature should be suitable to bring the reaction to completion at a minimum time, without the production of unwanted side products. In general, it is convenient to carry out the reaction at a temperature of from about 35° C. to about reflux temperatures of the reaction mixture or the solvents used. preferably at a temperature of from about 45° C. to about reflux temperatures. The time required for the reaction may also vary widely, depending on many factors, notably the reaction temperature and the nature of the reagent and solvent employed. However, provided that the reaction is effected under the preferred conditions discussed above, a period of from about 30 minutes to about 10 hours, preferably from about 1 hour to about 6 hours is sufficient.

The conversion of intermediate compound of formula V to the intermediate compound of formula II is also being performed using cuprous (I) salts as catalyst.

The cuprous (I) salts that can be used include but are not limited to cuprous chloride, cuprous bromide, cuprous iodide, cuprous cyanide and cuprous bromide-dimethyl sulphite. Preferably cuprous chloride.

The intermediate compound of formula II is optionally dried under conditions which avoid degradation of the product, which can be from about 25° C. to about 40° C. in the presence or absence of reduced pressure.

The processes reported for the preparation of Iloperdione or its intermediates results in the formation of various impurities and bye products leading to several purification steps thus resulting in very poor yields and purities of the intermediates and the final product.

Advantageously, the process of present invention provides the intermediate compound of formula II from novel intermediate compound of formula V and also further conversion to compound of formula I in higher yields and purities which inturn results in higher yields and purities of final product.

The intermediate compounds of formula II and V obtained by the process of present invention can be crystalline or amorphous form or mixture thereof.

The intermediate compounds of formula II, V and final compound of formula I are optionally purified by recrystallisation, using a solvent or mixture of solvents; such as methanol, ethanol, isopropyl alcohol, ethyl acetate, diethyl ether, methyl tertiary butyl ether, petroleum ether, n-hexane, n-heptane, cyclohexane, N,N-dimethyl formamide, acetone, acetonitrile or mixtures thereof or their aqueous mixtures.

The reaction time and the temperature should be suitable to bring the reaction to completion at a minimum time, without the production of unwanted side products. In general, it is convenient to carry out the reaction at a temperature of from about 35° C. to about 100° C. or boiling point of the solvent(s) used, preferably at a temperature of from about 50° C. to about 100° C. The time required for the reaction may also vary widely, depending on many factors, notably the reaction temperature and the nature of the reagent and solvent employed. However, provided that the reaction is effected under the preferred conditions discussed above, a period of from about 1 hour to about 10 hours, preferably from about 1 hour to 5 hours is sufficient.

After completion of the reaction, the desired compounds can be obtained from the reaction mixture by conventional means known in the art. For example, the working-up of reaction mixtures, especially in order to isolate desired compounds, follows customary procedures, known to the organic chemists skilled in the norms of the art and steps, e.g. selected from the group comprising but not limited to extraction, neutralization, crystallization, chromatography, evaporation, drying, filtration, centrifugation and the like.

The intermediate compound of formula II can be alternatively prepared by the processes as described in the examples herein.

The X in the compound of formula V is a leaving group selected from the group consisting of halogen (Cl, Br, I), methanesulphonate, benzene sulphonate, p-toluenesulphonate, 4-nitrobenzene sulphonate, 4-bromobenzene sulphonate and trifluoromethyl sulphonate. Preferably the X is chloro.

In another embodiment, the present invention provides a process for the preparation of Iloperidone of formula I

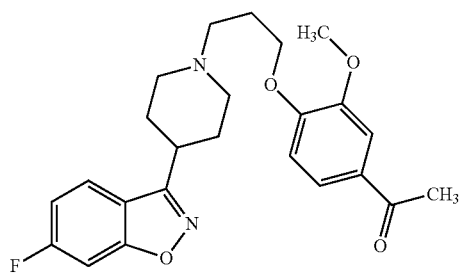

comprising:
reacting the intermediate compound 4-(3$^1$-propoxy)-3-methoxy acetophenone of formula (II)

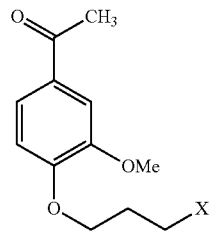

Where X is same as defined above.
with a compound 6-fluoro-3(4-piperidinyl)-1,2-benzisoxazole or a salt thereof of formula (IV)

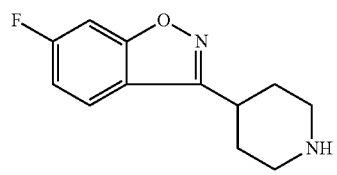

in the presence of a base and a solvent.

The base that can be used include organic base or inorganic base. The organic base is selected from the group consisting of triethylamine, tripropylamine, pyridine, diisopropylamine, diisopropylethylamine or mixture thereof. Inorganic bases include ammonia, sodium methoxide, sodium ethoxide, sodium tert-butoxide, potassium methoxide, potassium ethoxide, potassium tert-butoxide and the like; alkali metal carbonates such as sodium carbonate, potassium carbonate, sodium hydrogen carbonate and the like; and alkali metal hydroxides, such as sodium hydroxide, potassium hydroxide and the like or mixtures thereof, preferably potassium carbonate.

The solvents that can be used include but are not limited to water, halogenated solvents such as dichloromethane, ethylene dichloride, chloroform, chlorobenzene and the like; esters such as ethyl acetate, isopropyl acetate, tertiary butyl acetate and the like; hydrocarbon solvents such as n-heptane, cyclohexane, n-hexane, toluene, xylene and the like; ethers such as tetrahydrofuran, 1,4-dioxane and the like; aprotic polar solvents such as N,N-dimethylformamide (DMF), dimethylsulfoxide (DMSO), N,N-dimethylacetamide (DMA), N-methyl pyrrolidine (NMP) and the like; or mixtures thereof in various proportions without limitation. Preferably, N,N-dimethyl formamide (DMF) is being used.

The compound of formula IV can be used in the formed of acid addition salt preferably hydrochloric acid salt form is being used.

The molar ratio of compound of formula II and IV can be from about 0.25:2.5, preferably 1:1 is being used.

The reaction temperature and time should be suitable to bring the reaction to completion at a minimum time, without the production of unwanted side products. In general, it is convenient to carry out the reaction at a temperature of from about 35° C. to about 100° C. or boiling point of the solvent(s) used, preferably at a temperature of from about 50° C. to about 100° C. The time required for the reaction may also vary widely, depending on many factors, notably the reaction temperature and the nature of the reagent and solvent employed. However, provided that the reaction is effected under the preferred conditions discussed above, a period of from about 1 hour to about 10 hours, preferably from about 1 hour to 5 hours is sufficient.

After completion of the reaction, the desired compounds can be obtained from the reaction mixture by conventional means known in the art. For example, the working-up of reaction mixtures, especially in order to isolate desired compounds, follows customary procedures, known to the organic chemists skilled in the norms of the art and steps, e.g. selected from the group comprising but not limited to extraction, neutralization, crystallization, chromatography, evaporation, drying, filtration, centrifugation and the like.

In another embodiment, the present invention provides alternate process for the preparation of Iloperidone of formula I

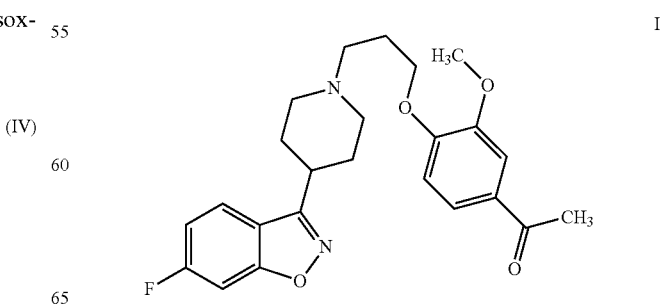

comprising:

a) reacting the intermediate compound 4-(3¹-Chloropropoxy)-3-methoxybenzonitrile of Formula (V)

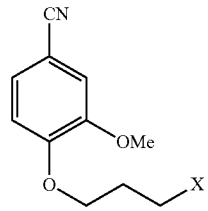

(V)

Where X is same as defined above.

with a compound 6-fluoro-3(4-piperidinyl)-1,2-benzisoxazole or a salt thereof of formula (IV)

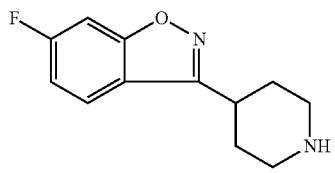

(IV)

in the presence of a base and an organic solvent to give 4'-[3-[4-(6-Fluoro-1,2-benzisoxazol-3-yl)piperidino]propoxy]-3'-methoxy benzonitrile of formula X

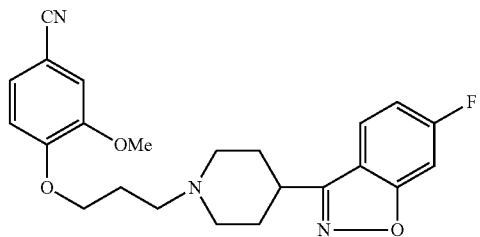

X b) reaction of the compound of formula X with Grignard reagent in the presence of catalyst cuprous (I) salts to afford compound of formula I.

The solvents that can be used in step a) include but are not limited to alcohols such as methanol, ethanol, isopropyl alcohol and the like; halogenated solvents such as dichloromethane, ethylene dichloride, chloroform, chlorobenzene and the like; esters such as ethyl acetate, isopropyl acetate, tertiary butyl acetate and the like; hydrocarbon solvents such as n-heptane, cyclohexane, n-hexane, toluene, xylene and the like; ethers such as tetrahydrofuran, 1,4-dioxane and the like; aprotic polar solvents such as N,N-dimethylformamide (DMF), dimethylsulfoxide (DMSO), N,N-dimethylacetamide (DMA), N-methyl pyrrolidine (NMP) and the like; or mixtures thereof in various proportions without limitation. Preferably, N,N-dimethyl formamide (DMF) is being used.

The base may include organic base or inorganic base. The organic bases that can be used include, but are not limited to triethylamine, tripropylamine, pyridine, diisopropylamine, diisopropylethylamine and the like, Inorganic bases include ammonia, alkali metal alkoxides such as sodium methoxide, sodium ethoxide, sodium tert-butoxide, potassium methoxide, potassium ethoxide or potassium tert-butoxide; alkali metal carbonates such as sodium carbonate or potassium carbonate, sodium hydrogen carbonate; and alkali metal hydroxides, such as sodium hydroxide or potassium hydroxide and the like or mixtures thereof, preferably potassium carbonate.

The reaction time and the temperature should be suitable to bring the reaction to completion at a minimum time, without the production of unwanted side products. In general, it is convenient to carry out the reaction at a temperature of from about 35° C. to about 100° C. or boiling point of the solvent(s) used, preferably at a temperature of from about 50° C. to about 100° C. The time required for the reaction may also vary widely, depending on many factors, notably the reaction temperature and the nature of the reagent and solvent employed. However, provided that the reaction is effected under the preferred conditions discussed above, a period of from about 1 hour to about 10 hours, preferably from about 1 hour to 5 hours is sufficient.

The solvents that can be used in step b) grignard reaction include but are not limited to halogenated solvents such as dichloromethane, ethylene dichloride, chloroform, chlorobenzene and the like; hydrocarbon solvents such as n-heptane, cyclohexane, n-hexane, toluene, xylene and the like; ethers such as diethyl ether, tetrahydrofuran, 1,4-dioxane and the like; or mixtures thereof in various proportions without limitation. Preferably, ether and toluene are being used.

The cuprous (I) salts that can be used in step b) include but are not limited to cuprous chloride, cuprous bromide, cuprous iodide, cuprous cyanide and cuprous bromide-dimethyl sulphite. Preferably cuprous chloride is being used.

The reaction temperature and time should be suitable to bring the reaction to completion at a minimum time, without the production of unwanted side products. In general, it is convenient to carry out the reaction at a temperature of from about 35° C. to about reflux temperatures of the reaction mixture or the solvents used. preferably at a temperature of from about 45° C. to about reflux temperatures. The time required for the reaction may also vary widely, depending on many factors, notably the reaction temperature and the nature of the reagent and solvent employed. However, provided that the reaction is effected under the preferred conditions discussed above, a period of from about 30 minutes to about 10 hours, preferably from about 1 hour to about 6 hours is sufficient.

In yet another embodiment, the present invention provides a process for purifying iloperidone comprising: a) providing a solution of iloperidone in a solvent or a mixture of solvents or their aqueous mixtures and b) precipitating the solid from the solution, and c) recovering the iloperidone in pure form.

The solvents include but are limited to water, alcohols such as methanol, ethanol, isopropanol and the like; ketones such as acetone, methyl ethyl ketone, ethyl methyl ketone and the like; nitriles such as acetonitrile, propionitrile and the like; hydrocarbons such as toluene, n-hexane, n-heptane, cyclohexane and the like; aprotic polar solvents such as N,N-dimethyl formamide (DMF), dimethyl sulfoxide (DMSO) and the like; ethers such as dimethyl ether, diethyl ether, isopropyl ether, methyl tertiary butyl ether (MTBE), tetrahydrofuran, 1,4-dioxane and the like; esters such as ethyl acetate, isopropyl acetate, isobutyl acetate, t-butyl acetate and the like; or mixtures thereof in various proportions without limitation. Preferably alcohols and water mixture.

The temperature for dissolution can range from about 25° C. to about 100° C. or reflux temperatures of the solvents used, preferably at about 30° C. The time period for dissolution can be range from about 30 minutes to about 5 hours, preferably 1 hour. The solution obtained is optionally filtered through celite or diatamous earth to separate the extraneous matter present or formed in the solution by using conventional filtration technique known in the art. The precipitation of solid in b) above is achieved but not limited to evaporation, cooling, drying, by adding antisolvent and the like.

The temperature range for precipitation of solid can be from about −10° C. to about 30° C., preferably about 0-5° C.

The time period for complete precipitation of solid can range from about 30 minutes to about 5 hours, preferably 1 hour.

Iloperidone obtained by the processes described can be dried can be from about 25° C. to about 75° C., preferably at about 50° C. and at reduced pressure of about e.g. 5 to 20 mbar, for a period of about 1 to about 10 hours. Preferably 1 hour.

In another embodiment, the present invention provides iloperidone obtained by the processes described herein above having purity greater than about 98.0 area % to about 99.0 area % as measured by HPLC, preferably greater than about 99.0 area % to about 99.5 area %, more preferably greater about 99.5 area % to about 99.8 area %.

In yet another embodiment, the present invention provides iloperidone obtained by the processes described herein above having individual impurities lower than about 0.15 area %, preferably lower than or equal to 0.1 area % and total impurities lower than about 0.5 area %, preferably lower than 0.25 area % as measured by HPLC.

In another embodiment, the present invention provides Iloperidone having the compound 4-hydroxy-3-methoxy benzaladehyde of structural formula VII

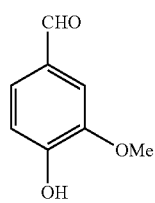

VII in an amount less than or equal to 0.10 area % as measured by HPLC.

In yet another embodiment, the present invention provides Iloperidone having the compound 4-(3-chloropropoxy)-3-methoxy benzaladehyde of structural formula VIII

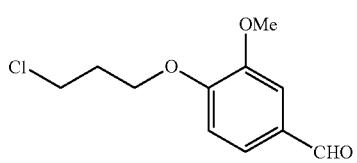

VIII in an amount less than or equal to 0.10 area % as measured by HPLC.

In a still further embodiment, the present invention provides Iloperidone having the compound 1-[4-(3-chloropropoxy)-3-methoxy phenyl]ethanone of structural formula IX

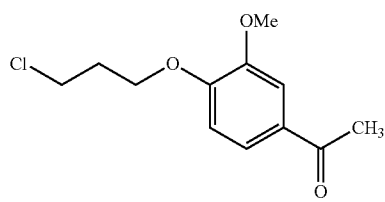

IX in an amount less than or equal to 0.10 area % as measured by HPLC.

In yet further embodiment, the present invention provides Iloperidone having the compound 6-fluoro-3-(4-piperidinyl)-1,2-benzisoxazole of structural formula IV

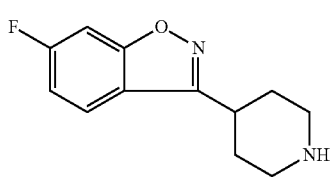

IV in an amount less than or equal to 0.10 area % as measured by HPLC.

Advantageously, Iloperidone obtained by the processes described above has residual organic solvents or organic volatile impurities comprises less than the amount recommended for pharmaceutical products, as set forth for example in ICH guidelines and U.S. pharmacopoeia; less than about 2000 ppm of methanol, ethanol, isopropanol, acetone, ethyl acetate, cyclohexane, diethyl ether, diisopropyl ether and dimethyl sulfoxide, less than about 500 ppm of dichloromethane, toluene and N,N-dimethyl formamide.

While the present invention has been described in terms of its specific embodiments, certain modifications and equivalents will be apparent to those skilled in the art and are intended to be included within the scope of the present invention.

EXAMPLES

Example-1

Preparation of 4($3^1$-chloropropoxy)-3-methoxy acetophenone using collins reagent as oxidizing agent (24.5 g, 0.245 moles) Chromium trioxide was added to a solution of 38.8 g (0.49 moles) of dry pyridine in 200 ml of dry dichloromethane and stirred for 15 minutes in a clean and dry 500 ml 4 neck R.B.Flask at about 30° C. A solution of the 1-[4-($3^1$-chloropropoxy)-3-methoxy phenyl]ethanol (10 g, 41 mmoles) in 100 ml of toluene was added in one portion. A tarry black deposit was separated immediately, after stirring for an additional 15 minutes at about 30° C., the solution was decanted from the residue, and washed with 100 ml of dichloromethane. The organic layers were combined and distilled completely under vacuum to obtain the residue. To the residue ether (100 ml) was added, filtered to remove insoluble chromium salts followed by washing with 5% cold aqueous sodium hydroxide solution and saturated brine solution. The solvent was evaporated under vacuum to afford the oily residue. To the oily residue 30 ml of diisopropyl ether was added and cooled to about 0° C. and stirred for 30 minutes. The solid separated was filtered and washed with chilled diisopropylether (10 ml) to give the title compound.
Yield: 8.15 gms (% Yield: 82%).

Example-2

Preparation of 4-(3'-methanesulfonyloxypropoxy)-3-methoxy acetophenone using collin's reagent as oxidizing agent Same procedure as described in Ex. 1 using 1-[4-(3'-methanesulfonyloxypropoxy)-3-methoxyphenyl]ethanol (12.5 gms (41 m·moles)) instead of 1-[4-(3'-chloropropoxy)-3-methoxy phenyl]ethanol to provide the title compound.
Yield: 10 gms (% Yield: 80%).

Example-3

Preparation of 4($3^1$-chloropropoxy)-3-methoxy acetophenone using DMSO-DCC as oxidizing agent (5 g, 20 mmoles) of 1-[4-($3^1$-chloropropoxy)-3-methoxy phenyl]ethanol in 20 ml of dimethylsulfoxide (DMSO) and toluene (70 ml) containing dicyclohexyl-carbodiimide (DCC) (12.4 g, 60 mmoles) were charged into a clean and dry 500 ml 4 neck R.B.Flask. Anhydrous orthophosphoric acid (0.4 ml of a 5M solution in dimethylsulfoxide (DMSO), 2 mmoles) was added, and the resultant reaction mixture was kept at about 30° C. for overnight. 100 ml of water was added and filtered after 30 minutes. The Filtrate was taken and washed the organic layer with 50 ml of aqueous hydrochloric acid solution and 50 ml of sodium bicarbonate solution and 50 ml of water. The solvent was distilled completely under reduced pressure and recrystallised from diisopropyl ether to give the title compound.
Yield: 2.2 gms (% Yield: 44%).

Example-4

Alternate process for the preparation of 4(3'-chloropropoxy)-3-methoxy acetophenone using DMSO-DCC as oxidizing agent 5 g (20 mmoles) of 1-[4-(3'-chloropropoxy)-3-methoxyphenyl]ethanol was dissolved in 20 ml of dimethylsulfoxide (DMSO) (20 ml) and toluene (70 ml) containing dicyclohexyl-carbodiimide (DCC) (12.4 g, 60 m·moles) were charged into a clean and dry 500 ml 4 neck R.B.Flask. Pyridine (1.58 g, 20 m·moles) and trifluoroacetic acid (0.8 ml, 10 m·moles) were added and the reaction mixture was kept at about 30° C. for overnight. Work up same as described in above example-3 to afford the title compound.
Yield: 2.45 gms (% Yield: 49%).

Example-5

Preparation of 4-(3'-benzenesulphonyloxy propoxy)-3-methoxy acetophenone using DMSO-DCC as oxidizing agent Same procedure as described in Ex. 4 using 1-[4-(3'-benzenesulphonyloxy propoxy)-3-methoxyphenyl]ethanol (7.32 gms (20 m·moles) instead of 1-[4-(3'-chloropropoxy)-3-methoxyphenyl]ethanol to provide the title compound.
Yield: 3.6 gms (% Yield: 49%).

Example-6

Preparation of 4($3^1$-chloropropoxy)-3-methoxy acetophenone using DMSO-Acetic anhydride as oxidizing agent 5 g (20 mmoles) of 1-[4-($3^1$-chloropropoxy)-3-methoxyphenyl]ethanol dissolved in 130 ml of dimethyl sulfoxide (DMSO) and 40 ml of acetic anhydride were charged in a clean and dry 500 ml R.B.Flask and stirred at about 30° C. for overnight. acetic anhydride was evaporated under vacuum leaving a residue which was dissolved in ethyl acetate, washed with aqueous sodium bicarbonate solution, and then with water, and dried over sodium sulphate. After evaporation of the solvent the residue was crystallized from diisopropylether to give the title compound.
Yield: 3.2 gms (% Yield: 64.5%).

Example-7

Preparation of 4-(3'-benzenesulphonyloxy propoxy)-3-methoxy acetophenone using DMSO-Acetic anhydride as oxidizing agent Same procedure as described in Ex. 6 using 1-[4-(3'-benzenesulphonyloxy propoxy)-3-methoxyphenyl]ethanol (7.32 gms (20 m·moles) instead of 1-[4-(3'-chloropropoxy)-3-methoxyphenyl]ethanol to give the title compound.
Yield: 4.7 gms (% Yield: 64.5%).

Example-8

Preparation of 1-[4-($3^1$-benzenesulphonyloxy propoxy)-3-methoxyphenyl]ethanol

Magnesium turnings (4.8 g, 0.2 moles) and ether (100 ml) were charged in a clean and dry 500 ml 4 neck R.B.Flask and stirred to make a suspension. methyl iodide (35.5 g, 0.25 moles) was added to the suspension by drop-wise. The resultant reaction mixture was refluxed for 30 minutes and cooled to about 0° C. 4-($3^1$-benzenesulphonyloxypropoxy)-3-methoxy benzaldehyde (35 g, 0.1 moles) dissolved in 100 ml toluene was added under cooling by drop-wise. The resultant reaction mixture was raised heated to room temperature and stirred for 4 hours at 25-30° C. Decomposed the reaction mixture into ice and acidified with aqueous sulfuric acid. Separated the organic layer and aqueous layer extracted into toluene (50 ml×2). The organic layer washed with water (50 ml) followed by brine solution (50 ml) and distilled completely under reduced pressure to yield the title compound as yellow oil. Yield: 30 gms.

Example-9

Preparation of 4($3^1$-chloropropoxy)-3-methoxy acetophenone using pyridinium chlorochromate as oxidizing agent (13.5 g, 63 mmol) pyridinium chlorochromate (PCC) and 100 ml of anhydrous dichloromethane were charged into a clean and dry 500 ml 4 neck RB Flask. 1-[4-($3^1$-chloropropoxy)-3-methoxy phenyl]ethanol (10 g, 41 mmol) in 100 ml of toluene was charged at about 30° C. The resultant reaction mixture was stirred for about 1 hour 30 minutes and 100 ml of dichloromethane was added and the supernatant solution was decanted from the black gum. The solvent was distilled completely under vacuum to get an oily residue. To the residue 30 ml of diisopropylether was added to give the title compound.
Yield: 8 gms (% Yield: 80%).

Example-10

Preparation of 4-(3$^1$-chloropropoxy)-3-methoxy acetophenone using pyridinium chlorochromate as oxidizing agent 23.1 ml of 6M hydrochloric acid was charged in clean and dry 500 ml 4 neck R.B.Flask followed by addition of 12.5 g of chromium (VI) oxide under stirring. After 5 min. the homogenous solution was cooled to about 0° C. and 12.25 ml of pyridine was added over 10 min. The orange-yellow precipitate was heated to about 30° C. and 1-[4-(3'-chloropropoxy)-3-methoxy phenyl]ethanol (10 g) (41 mmol) in 200 ml toluene was added at once. After 2 hours of stirring at about 30° C., the organic phase was separated and the aqueous phase was extracted with toluene (2×50 ml). The organic layers were combined and washed with water (2×50 ml). The organic layer was separated and distilled completely to get an oily residue and recrystallised from diisopropylether to give the title compound.
Yield: 7.8 gms Example-11

Preparation of 4-(3$^1$-benzenesulfonyloxypropoxy)-3-methoxy acetophenone using pyridinium chlorochromate as oxidizing agent Same procedure as described in Ex. 10 using 1-[4-(3'-benzenesulfonyloxypropoxy)-3-methoxy phenyl]ethanol (15 g, 41 mmol) to give the title compound.
Yield: 12.5 gms (% Yield: 84%).

Example-12

Preparation of 4-(3'-chloro propoxy)-3-methoxy acetophenone using pyridinium chlorochromate on alumina as oxidizing agent (7.5 gr., 6.1 m·moles) pyridinium chlorochromate on alumina reagent was added to a flask containing a solution of 1-[4-(3'-chloropropoxy)-3-methoxyphenyl]ethanol (9.3 gr., 38 m·moles) in 100 ml. toluene and stirred for about 2 hrs. The reaction solution was filtered, and washed with (3×10 ml.) of toluene. The combined filtrates were evaporated and recrystallized from aqueous methanol to yield the title compound.

Example-13

Preparation of 4-(3'-chloropropoxy)-3-methoxy acetophenone using pyridinium dichromate as oxidizing agent 30.75 gr. (81.8 m·mol) of pyridinium dichromate and 75 ml. of dichloromethane were charged into a clean and dry 500 ml 4 neck R.B.Flask. 10 gr. (41 m·mol) of 1-[4-(3'-chloropropoxy)-3-methoxy phenyl]ethanol in 100 ml. of toluene was added in one portion. The resulted reaction mixture was stirred at about 30° C. for about 4 hrs. The chromium salts separated were filtered and washed with 50 ml. of toluene. The filtrate was washed with water (2×50 ml) and distilled completely under vacuum to furnish the oily residue. To the oily residue, 30 ml. of di-isopropyl ether was added and cooled to about 0° C. and stirred for about 30 min. The separated solid was filtered and the solid obtained was washed with 10 ml. of chilled di-isopropyl ether to afford the title compound.
Yield: 7.72 gms (% Yield: 77%).

Example-14

Preparation of 4-(3'-p-toluenesulfonylpropoxy)-3-methoxy acetophenone using pyridinium dichromate as oxidizing agent Same procedure as described in Ex. 13 using 1-[4-(3'-p-toluenesulfonyloxypropoxy)-3-methoxyphenyl]ethanol (5.6 gms (41 m·moles)) to provide 12 gr. of the title compound as an off-white crystalline powder.
Yield: 12 g (% Yield: 78%).

Example-15

Preparation of 4-(3$^1$-Chloropropoxy)-3-methoxybenzonitrile (V)

114.2 gms (0.5 moles) of 4-(3$^1$-chloropropoxy)-3-methoxy benzaldehyde (VI) was dissolved in 200 ml. of preheated 95% alcohol in a clean and dry R.B.Flask. To the resultant reaction solution a warm solution of 42 gms (0.6 mol.) of hydroxylamine hydrochloride in 50 ml. of water was added. The two solutions were mixed thoroughly, and a solution of 30 gms (0.75 mol.) of sodium hydroxide in 40 ml. of water was added drop-wise. The resultant reaction mixture was stirred at about 30° C. for about 2 hours 30 minutes. The separated white crystalline solid was filtered and the solid was washed with copious amount of water. The obtained intermediate oxime was suspended in 100 gms of acetic anhydride and heated to reflux for about 30 minutes. After completion of the reaction, the reaction mixture was quenched by adding to 300 ml of ice-cold water slowly under stirring. The solid separated was filtered and the solid obtained was washed with copious amount of water. The solid obtained was recrystallised from 300 ml of methanol using decolourising carbon to afford the title compound.
Yield: 84.5 gms (% Yield: 75%).

Example-16

Preparation of 1-[4-(3$^1$-Chloropropoxy)-3-methoxyphenyl]ethanone (II)

(10.6 gr., 0.44 moles) Magnesium turnings and 100 ml. diethyl ether were charged in a clean and dry 1 lilt. 4 neck R.B.Flask. 78.7 gms (0.55 moles) of methyl iodide in 100 ml. of ether was added at about 20° C. (after addition of 4-5 gr. Of methyl iodide initiation started). The resultant reaction mixture was refluxed for about 30 min. To the resultant suspension 1 liter of toluene was added and the solvent was distilled to a volume of about 200 ml. Then 50 gms (0.22 moles) of 4-(3'-chloropropoxy)-3-methoxybenzonitrile in 250 ml of toluene was added and the resultant reaction mixture was refluxed for about 3 hrs. The reaction mixture was cooled to about 0° C. and 800 ml. of 10% HCl solution was added drop-wise. The resultant reaction mixture was refluxed for about 6 hrs. The reaction mixture was cooled and the organic layer was separated. The organic layer was washed with 200 ml of 10% w/v sodium carbonate solution followed by 200 ml of water. The organic layer was separated and the solvent was distilled-off completely under vacuum to afford the residue. The residue was re-crystallized from 200 ml of di-isopropyl ether to afford the title compound as an off-white crystalline solid.

Yield: 37.6 gms (% Yield: 75%).

Example-17

Preparation of 1-[4-(3'-p-Toluenesulfonyloxypropoxy)-3-methoxy phenyl]ethanone

Same procedure as described in Ex. 16 using 4-(3'-p-toluene sulfonyloxy propoxy)-3-methoxybenzonitrile (79.4 gms (0.22 moles) and the solid was recrystallized from methanol to give the title compound.

Yield: 36.8 gms (% Yield: 44.3%).

Example-18

Alternate process for the preparation of 1-[4-(3$^1$-Chloropropoxy)-3-methoxyphenyl]ethanone (II)

To a 3 molar solution of methyl magnesium iodide in diethyl ether (86.3 gms (0.26 mol) added 30 gms (0.13 mol) of 4-(3$^1$-chloropropoxy)-3-methoxybenzonitrile in 300 ml of anhydrous toluene and 230 mg (2.32 mmol) of cuprous chloride and the resultant reaction mixture was refluxed under nitrogen for about 1 hr. The reaction mixture was cooled to about 25-30° C. and 50 ml of water was added slowly for about 15 minutes followed by addition of 332 ml of (15% v/v) sulphuric acid. The reaction mixture was stirred for about 2 hours under reflux, 100 ml of toluene was added. Organic and aqueous layers were separated and the aqueous layer was extracted with 100 ml of toluene. The organic layers were combined and washed with 100 ml of 10% w/v sodium carbonate solution and then with 100 ml of water. The solvent was distilled completely under vacuum and the residue was re-crystallized from 200 ml of di-isopropyl ether to afford the title compound as an light brown coloured solid.

Yield: 25 gms (% Yield: 77.5%).

Example-19

Alternate process for the preparation of 1-[4-(3$^1$-Chloropropoxy)-3-methoxyphenyl]ethanone (II)

To a 3 molar solution of methyl magnesium iodide in diethyl ether (49.8 gms (0.15 mol) added 30 gms (0.13 mol) of 4-(3$^1$-chloropropoxy)-3-methoxybenzonitrile in 300 ml of anhydrous toluene and 230 mg (2.32 mmol) of cuprous chloride and the resultant mixture was refluxed under nitrogen for about 2 hrs. The reaction mixture was cooled to about 25-30° C. and 50 ml of water was added slowly for about 15 minutes followed by addition of 332 ml of (15% v/v) sulphuric acid. The reaction mixture was stirred for about 2 hours under reflux, 100 ml of toluene was added. Organic and aqueous layers were separated and the aqueous layer was extracted with 100 ml of toluene. The organic layers were combined and washed with 100 ml of 10% w/v sodium carbonate solution and then with 100 ml of water. The solvent was distilled completely under vacuum and the residue was re-crystallized from 200 ml of di-isopropyl ether to afford the title compound as an light brown coloured solid. Yield: 24 gms (74.4%).

Example-20

Alternate process for the preparation of 4-(3$^1$-Chloropropoxy)-3-methoxy benzonitrile (V)

To 2.28 gms (0.01 mole) of 4-(3'-Chloropropoxy)-3-methoxy benzaldehyde, 0.8 gms (0.015 moles) of hydroxylamine hydrochloride, 1.25 gms of sodium formate and 15 ml (98-100%) of formic acid were added and the resultant reaction mixture was refluxed for about 1 hr. The title compound was obtained by dilution with water as a colourless crystals.

Yield: 2.1 gms (% Yield: 93%).

Example-21

Alternate process for the preparation of 4-(3'-Chloropropoxy)-3-methoxybenzonitrile (V)

To 74.5 gms (0.5 mole) of 4-Hydroxy-3-methoxybenzonitrile in 450 ml. of acetone was added 138 gms (1 mole) of potassium carbonate and the resultant reaction mixture was stirred at about 25-30° C. for about 5 min. To the reaction suspension 110 gms (0.7 mole) of 3-Chloro-1-bromo propane was added drop-wise at about 25-35° C. for about 30 mins. The resultant reaction mixture was refluxed for about 12 hrs. The undissolved inorganic salts was filtered off and washed with acetone. The solvent was distilled completely under vacuum and the residue was re-crystallized from 300 ml of isopropyl alcohol to afford the title compound as white crystalline solid. Yield: 92.5 gms (% Yield: 82%).

Example-22

Preparation of 4-(3'-p-toluenesulfonyloxypropoxy)-3-methoxy benzonitrile

Step-1:

To 74.5 gr. (0.5 mole) of 4-Hydroxy-3-methoxy benzonitrile in 450 ml. of acetone, was added 136 gms (1 mole) of potassium carbonate and stirred at about 25-30° C. for about 5 min. To the resultant reaction suspension 97.3 gms (0.7 mole) of 3-bromo-1-propanol was added by drop-wise at about 25-35° C. and refluxed the mixture for about 12 hrs. The separated inorganic salts were filtered off and washed with acetone. The solvent was distilled completely under vacuum and the solid obtained was recrystallized from isopropyl alcohol to afford the intermediate compound.

Step-2:

To 50 gms (0.24 mole) of 4-(3'-Hydroxypropoxy)-3-methoxy benzonitrile in 200 ml. of cyclohexane was added 26 gms (0.24 mole) of sodium carbonate and 46 gms (0.24 mole) of p-toluene sulfonyl chloride at once. The resultant reaction mixture was refluxed for about 4-6 hrs. After completion of the reaction, the reaction mass was cooled to about 25-30° C. and the inorganic salts were filtered off. and washed with cyclohexane. The solvents were distilled completely and solid obtained was recrystallized from 150 ml of ethyl acetate to afford the title compound as white crystalline powder.

Yield: 60.5 gms (% Yield: 75%).

Example-23

Preparation of Iloperidone (I)

4-(3'-p-toluene sulfonyloxy propoxy)-3-methoxy acetophenone (37.8 g, 0.1 moles), sodium carbonate (42.4 g, 0.4 moles) and 220 ml of N,N-dimethylformamide (DMF) were charged in a clean and dry 500 ml 4 neck R.B.Flask. 6-fluoro-3(4-piperidinyl)-1,2-benzisoxazole hydrochloride (25.5 g, 0.1 moles) was added at about 65° C. and stirred for about 8 hrs. After completion of the reaction, the reaction mixture was quenched by pouring into water and filtered after 30 minutes. The solid obtained was recrystallized from aqueous methanol to get pure Iloperidone (I) as white crystalline powder.

Example-24

Alternate Process for the Preparation of Iloperidone (I)

6-Fluoro-3-(4-piperidinyl)-1,2benzisoxazole hydrochloride (IV) (25.5 gr., 0.1 mol.), potassium carbonate (27.0 gr., 0.2 mol.) and 80 ml. of N,N-dimethyl formamide (DMF) were charged into a clean and dry 500 ml 4 neck R.B.Flask. 4-(3'-chloropropoxy)-3-methoxybenzonitrile (V) (20.0 gr., 0.08 mol.) and potassium iodide (680 mg.) were added at about 30° C. The resultant reaction mixture was heated to about 90° C. and stirred for about 9 hrs. After completion of the reaction, the reaction mixture was cooled to about 30° C. and 400 ml. of water were charged. After stirring for 30 min., the separated solid was filtered and the solid obtained and washed with 50 ml. of water. Recrystallized from methanol and water (3:1) using decolourising carbon to afford the title compound as an off-white crystalline powder. Yield: 28.4 gr (% Yield: 78%).

40.95 gr. (0.1 mol.) of 4'-[3-[4-(6-Fluoro-1,2-benzisoxazol-3-yl)-piperidino]-propoxy]-3'-methoxy benzonitrile (X) in 400 ml. of toluene was added to a 3.0 molar solution of methyl magnesium iodide (66.4 gr., 0.2 mol.) in diethyl ether taken in a clean and dry 1 lit. 4 neck R.B.Flask at once. 309 mg. of cuprous chloride was added and the resultant reaction mixture was quickly heated to reflux and stirred for about 2 hrs. The reaction mixture was cooled to about 25° C., 50 ml. of water was added followed by addition of 350 ml. of 15% v/v sulphuric acid solution. The resultant reaction mixture was heated to reflux for about 2 hrs. The reaction solution was cooled to about 30° C., and the organic layer was separated and the aqueous layer was extracted with toluene (2×100 ml.). The organic layers were combined and washed with 200 ml. of 10% w/v sodium carbonate solution followed by 200 ml. of water. The solvent was distilled-off completely under vacuum to yield Iloperidone as a yellow oil which was solidified upon standing. The product was recrystallized from methanol and water (3:1) by using decolourising carbon to afford Iloperidone as an off-white crystalline powder.

Yield: 29.8 gr. (% Yield: 70%).

Purification Processes

Example-1

Purification of Iloperidone (I) Using Methanol:Water (1:1)

42.5 gms of crude Iloperidone was dissolved in a mixture of 744 ml of methanol and 319 ml of water at reflux. 8 gms of charcoal carbon was charged and filtered hot on celite. The reaction solution was cooled to about 25-30° C. and 425 ml. of water was added followed by stirring for about 30 min. The separated solid was filtered and the solid was washed with 50 ml. of methanol-water mixture (1:1) to afford pure form of Iloperidone as a cream-light yellow solid.

Yield: 32 gms (% Yield: 75%); Purity by HPLC: 99.75%.

Example-2

Purification of Iloperidone (I) Using Methanol:Water (3:1)

32 gms of Iloperidone (obtained in Ex. 1) were dissolved in a mixture of methanol (600 ml.) and water (200 ml) at reflux. 6 gms of charcoal carbon was charged under reflux and the resultant suspension was filtered hot on celite. The filtrate was cooled to about 25-30° C. and stirred for about 20 min. The solution was further cooled to 0-5° C. and stirred for about 30 min. The separated solid was filtered and the solid was washed with 50 ml of precooled methanol to afford pure Iloperidone as a white solid.

Yield: 24 gms (% Yield: 56%); Purity by HPLC: 99.8%.

Example-3

Purification of Iloperidone (I) Using Ethyl Acetate 42.5 gms of crude Iloperidone was dissolved in ethyl acetate (212.5 ml.) at reflux. 8 gms of charcoal carbon was charged under reflux. The suspension was filtered hot on celite. The filtrate solution was cooled to about 0-5° C. and stirred for 30 min. The separated solid was filtered and the solid obtained was washed with 40 ml of precooled ethyl acetate to afford 34 gms of pure form of Iloperidone as a light brown solid.

Yield: 34 gms; Purity by HPLC: 99.5%.

Example-4

Purification of Iloperidone (I) Using Toluene 42.5 gms of crude Iloperidone was dissolved in 212 ml of toluene at reflux. 8 gms of charcoal carbon was charged and the suspension was filtered hot on celite. The filtrate solution was cooled to about 25-30° C. followed by further cooling to about 0-5° C., stirred for 30 min. The separated solid was filtered and the solid washed with 40 ml of precooled toluene to afford 29.7 gms of pure form of Iloperidone as a light-yellow solid.

Yield: 29.7 gms; Purity by HPLC: 99.5%.

Example-5

Purification of Iloperidone (I) Using Dimethyl Formamide-Water 42.5 gms of crude Iloperidone was dissolved in a mixture of 212.5 ml of N,N-dimethylformamide (DMF) and 212.5 ml of water by heating to about 90° C. 8 gms of charcoal carbon was charged and filtered hot and the filtrate was cooled to about 25-30° C. and stirred for about 30 min. The separated solid was filtered and the solid was washed with a mixture of N,N-dimethyl formamide (DMF) and water (1:1) (50 ml.) to afford Iloperidine in pure form as a light-brown solid.

Yield: 30.6 gms; Purity by HPLC: 99.7%.

Example-6

Purification of Iloperidone (I) Using Acetone 42.5 gms of crude Iloperidone was dissolved 170 ml of acetone at reflux. 8 gms of charcoal carbon was charged, the resultant suspension was filtered hot and the filtrate was cooled to about 25-30° C. and stirred for about 5 min. The filtrate was further cooled to about 0-5° C. and stirred for about 30 min. The separated solid was filtered and the solid was washed with 40 ml of precooled acetone to afford 29.7 gms of Iloperidone in pure form as a light-yellow crystals. Purity by HPLC: 99.5%.

Example-7

Purification of Iloperidone (I) Using Methanol:Water (3:1)

29.7 gms of Iloperidone was dissolved in a mixture of 556 ml of methanol and 188 ml of water at reflux. 6 gms of charcoal carbon was charged and the resultant suspension was filtered hot. The filtrate was cooled to about 25-30° C. followed by further cooling to about 0-5° C. and stirred for about 30 min. The separated solid was filtered and the solid was washed with 30 ml of precooled methanol to afford Iloperidone in pure form as a white crystalline solid.

Yield: 22.2 gms; Purity by HPLC: 99.4%.

Example-8

Purification of Iloperidone (I) Using Ethanol 42.5 gms of crude Iloperidone was dissolved 340 ml of ethanol at reflux. 8 gms of charcoal carbon was charged and the resultant suspension was filtered hot on celite. The filtrate was cooled to about 25-35° C. followed by further cooling to about 0-5° C., stirred for about 30 min. The separated solid was filtered and the solid was washed with 80 ml of precooled ethanol to give 34 gms of Iloperidone as a light-brown solid. Repeated the same crystallization with 34 gr. of Iloperidone in 272 ml. of ethanol to obtain pure Iloperidone as a white crystalline solid.

Yield: 25.5 gr. (% Yield: 60% based on theoretical weight); Purity by HPLC: 99.6%.

We claim:

1. A process for preparing intermediate 4-($3^1$-propoxy)-3-methoxyacetophenone compound of formula (II):

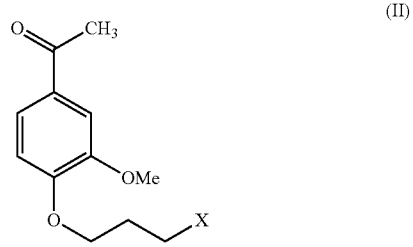

wherein X is a leaving group selected from halogen, methanesulphonate, benzenesulphonate, p-toluenesulphonate, 4-nitrobenzene sulphonate, 4-bromobenzene sulphonate and trifluoromethyl sulphonate, comprising:
reacting 1-[4-($3^1$-propoxy)-3-methoxyphenyl]ethanol of formula (III):

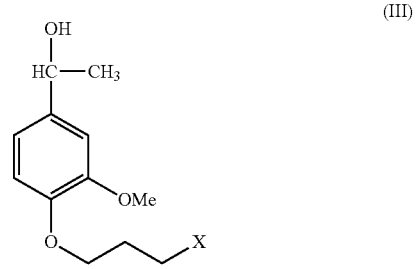

where X is as defined above;
with an oxidizing agent, optionally in the presence of a solvent, wherein the oxidizing agent is selected from the group consisting of collin's reagent, pyridinium dichromate, pyridinium chlorochromate, pyridinium chlorochromate on alumina, DMSO-DCC, DMSO-acetic anhydride or mixtures thereof.

2. A The process of claim 1, wherein the oxidizing agent is selected from the group consisting of collin's reagent, pyridinium dichromate, DMSO-DCC or DMSO-acetic anhydride.

3. A process of claim 1, wherein the solvent is selected from the group consisting of water, dichloromethane, ethylene dichloride, chloroform, chlorobenzene, n-heptane, cyclohexane, n-hexane, toluene, zylene, tetrahydrofuran, 1,4-dioxane, N,N-dimethylformamide (DMF), dimethylsulfoxide (DMSO), N,N-dimethylacetamide (DMA), N-methyl pyrrlolidine (NMP) and mixtures thereof.

4. The process of claim 1, wherein the reaction is carried out optionally in the presence of an acid.

* * * * *